(12) United States Patent
Kyriakis

(10) Patent No.: US 9,733,193 B2
(45) Date of Patent: Aug. 15, 2017

(54) MEASUREMENT OF INDUSTRIAL PRODUCTS MANUFACTURED BY EXTRUSION TECHNIQUES

(71) Applicant: Proton Products International Limited, Beaconsfield, Buckinghamshire (GB)

(72) Inventor: John Kyriakis, Beaconsfield (GB)

(73) Assignee: Proton Products International Limited, Buckinghamshire (GB)

( * ) Notice: Subject to any disclaimer, the term of this patent is extended or adjusted under 35 U.S.C. 154(b) by 187 days.

(21) Appl. No.: 14/656,106

(22) Filed: Mar. 12, 2015

(65) Prior Publication Data

US 2016/0265901 A1    Sep. 15, 2016

(51) Int. Cl.
| | |
|---|---|
| *G01B 11/10* | (2006.01) |
| *G01N 21/86* | (2006.01) |
| *G01B 11/04* | (2006.01) |
| *G01B 11/06* | (2006.01) |
| *G01B 11/24* | (2006.01) |

(Continued)

(52) U.S. Cl.
CPC ........... *G01N 21/86* (2013.01); *G01B 11/046* (2013.01); *G01B 11/0616* (2013.01); *G01B 11/0691* (2013.01); *G01B 11/10* (2013.01); *G01B 11/2433* (2013.01); *G01N 21/3581* (2013.01); *G01N 21/952* (2013.01)

(58) Field of Classification Search
CPC ...................................................... G01N 11/00
See application file for complete search history.

(56) References Cited

U.S. PATENT DOCUMENTS

| | | |
|---|---|---|
| 3,496,373 A | 2/1970 | Thorman et al. |
| 3,765,774 A | 10/1973 | Petrohilos |

(Continued)

FOREIGN PATENT DOCUMENTS

| | | |
|---|---|---|
| DE | 10309845 A1 | 9/2004 |
| DE | 102006048433 | 6/2008 |

(Continued)

OTHER PUBLICATIONS

EP Search Report dated May 13, 2014 of Patent Application No. EP13005999.1 filed Dec. 22, 2013.

*Primary Examiner* — David Porta
*Assistant Examiner* — Jeremy S Valentiner
(74) *Attorney, Agent, or Firm* — Maine Cernota & Rardin

(57) ABSTRACT

The invention relates to apparatus for monitoring an extruded product moving in an inline extrusion process so as to effect quality control of the process by continuously measuring dimensional parameters and determining the existence of contaminants in the extrusion. The apparatus makes use of Terahertz radiation which is adapted to provide a curtain of parallel rays of the radiation which is scanned across the product as the product passes therethrough in a linear manner. The composition of the emitted radiation received after the scanning process is subject to an imaging analysis to determine the dimensional parameters of the moving products. The imaging analysis involves applying correction values to the measured transit times of the rays crossing the products which depends on its position within the curtain of rays thereby to remove inaccuracies in the final measurement results.

10 Claims, 11 Drawing Sheets

(51) Int. Cl.
 *G01N 21/3581* (2014.01)
 *G01N 21/952* (2006.01)

(56) References Cited

U.S. PATENT DOCUMENTS

| | | | | |
|---|---|---|---|---|
| 4,208,126 | A | * | 6/1980 | Cheo .................... G01N 21/952 250/341.1 |
| 5,687,209 | A | * | 11/1997 | Adams ................. G01N 23/046 378/22 |
| 2002/0067480 | A1 | | 6/2002 | Takahashi |
| 2008/0197286 | A1 | * | 8/2008 | Kasai ................. G02B 26/0808 250/341.1 |
| 2009/0101823 | A1 | | 4/2009 | Jez et al. |
| 2009/0128799 | A1 | * | 5/2009 | MacHattie ........... D21G 9/0036 356/5.05 |
| 2010/0148069 | A1 | * | 6/2010 | Ouchi ................. G01N 21/4795 250/341.8 |
| 2011/0046768 | A1 | * | 2/2011 | Rayzak .................. H01B 3/441 700/103 |
| 2012/0209536 | A1 | * | 8/2012 | Hughes ............. G01N 21/3563 702/28 |
| 2012/0260743 | A1 | * | 10/2012 | Hersche ............... G01N 21/359 73/861.351 |

FOREIGN PATENT DOCUMENTS

| | | | |
|---|---|---|---|
| EP | 0443322 | A2 | 8/1991 |
| EP | 0828143 | A2 | 3/1998 |
| EP | 1930714 | A2 | 6/2008 |
| EP | 2116838 | A1 | 11/2009 |
| GB | 1458594 | | 12/1976 |
| GB | 14588828 | | 12/1976 |
| GB | 2132343 | A | 12/1982 |
| GB | EP 0686828 A1 * 12/1995 ........... G01B 15/025 |
| JP | 2002243416 | A | 8/2002 |
| JP | 2010261902 | A | 11/2010 |
| WO | 2009062315 | A1 | 5/2009 |
| WO | 2009117826 | A1 | 10/2009 |

* cited by examiner

MEASUREMENT OF INDUSTRIAL PRODUCTS MANUFACTURED BY EXTRUSION TECHNIQUES

FIELD OF THE INVENTION

The present invention relates to the non-contact measurement of the dimensional properties of elongated linearly extruded products such as rubber or plastic tubing, pipes and electrical cables with metallic conductor cores coated with a non-metallic insulating extruded material. It also relates to the measurement of manufactured flat products, such as rubber or plastic sheets, insulating tape, films, paper and the like.

BACKGROUND OF THE INVENTION

Linearly extruded products of the type referred to above are usually manufactured in an extrusion line typically comprising a pay-off device, an extrusion machine, a cooling section and a take-up device for the completed product.

In continuous manufacturing processes of this type, to which the present invention relates, it is a requirement to measure the diameter and wall thickness of the extruded products such as tubes or pipes and, in the case of electrical cables, the eccentricity also, that is the off-set position with respect to coaxiality of the metallic core within the insulating coating of the cables.

The need to monitor these measurements on a continuous basis in an extrusion process is, firstly, to ensure specification conformity and, secondly, that the extruded material is being applied as economically as possible in terms of using only that amount of extrusion material absolutely necessary, thus avoiding waste.

In the prior art available at the time the present invention was conceived, these measurements were carried out by optical means using white light or laser light, but these processes are only capable of measuring the overall diameter of the extruded product. By the use of more than one device, it is possible to measure indirectly wall thickness and eccentricity. Ultra-sonic methods have also been used to measure wall thickness using water as a contact medium.

The use of radioactive beta or x-rays enables the measurement of the wall thickness of an extruded product without contact with it. These methods, however, require special handling by reason of the fact that they involve inherent health hazards as will be readily appreciated.

The invention may also be used in the industrial field of manufacturing flat products, such as, rubber or plastic sheets, insulating tapes, films, paper and the like, thereby to measure the thickness of the material and the overall width of the product being manufactured.

Prior art available in measuring flat products, includes indirect contact methods, whereby two wheels or rollers are placed above and below the product, and the difference of the readings shown by the two wheels, indicates product thickness.

A non-contact optical method has also been used, in which, two "distance measuring devices" are mounted above and below the product. The difference between the two distance readings indicates product thickness.

Both these methods suffer from inaccuracies, which include mechanical wear and wheel bounce in the case of the mechanical contact type and defocussing on the optical type, either on product vibration or product thickness change.

A further limitation of the "contact" and "optical" methods is that they measure, only the thickness along a narrow part of the product width and not the complete area of the flat product sheet.

Alternative measuring methods such as, ultrasonic, radioactive, beta or x-rays are not recommended, since they require special handling and therefore present an inherent health hazard as will be appreciated.

The present invention makes use of terahertz radiation (hereinafter referred to as THz radiation) to irradiate the product as it passes through the rays on its path of travel and to utilize in a time related manner the radiation after passing through the product to determine its dimensional profile.

The frequencies of THz radiation are located between infra-red and micro-waves and the wavelengths of THz radiation are in the range between 30 micrometers and 3 millimeters.

Terahertz radiation (THz) has the advantage in that it behaves in a manner similar to that of white light, that is to say that the radiation can be reflected by mirrored surfaces but is able to penetrate and pass through dielectric or insulating materials such as rubber, paper and various plastics including polyethylene and the like.

The speed of transmission of THz radiation through the dielectric or insulating material is dependent on the chemical composition and material density of the product and this property and a penetrative ability of the THz radiation through dielectric or insulated materials will be used to obtain the measurements required.

The system disclosed herein utilizes an optical system to produce a curtain of THz radiation through which the product passes in a linear fashion in its path of travel.

The transient time or speed of each successive ray in the curtain of rays is used to compute, by matrix imaging methods, the dimensional parameters of the product in particular to determine the thickness of the extrusion coating so as to ensure that the coating thickness meets operational requirements.

Uniformity of the transient times or speeds of the rays through the extruded coating are important in achieving high accuracy of the results of the measuring process.

Due to the optical components of the system in that some rays in the curtain will be travelling at different speeds than others, these transient times or speeds will differ so that the accuracy of the results obtained will vary in dependence on the position of the products in the curtain of rays which occurs due to the swaying motion of the product in its path of travel.

SUMMARY OF THE INVENTION

It is an object of the present invention to obviate the problem with the optical measuring system as just described above by introducing into the measuring technique the capability to compensate for inaccuracies in transient times of the THz radiation through the extruded coating as the product moves transversely to the direction of the curtain of rays so that the results obtained are more accurate than heretofore obtainable.

According to one aspect of the present invention there is provided an apparatus for measuring by non-contact, the dimensional parameters of an elongated, non-guided industrial product such as a rubber or plastic tube or electrical cable, being extruded continuously in free space, comprising a terahertz radiation unit, a rotating mirror for scanning terahertz rays emitted from a point source across a first lens to produce a curtain of parallel terahertz rays, through which the product travels linearly at right angles thereto, the rays after passing through the insulating material being collected by a second lens, and focused at a terahertz sensor, an image analyser operatively associated with the sensor for performing time related imaging analysis of terahertz rays penetrating the insulating material to provide a matrix image from which to determine the dimensional parameters of the product characterised in that the analyser incorporates a processor for computing correction data representative of variation in the transit times between the rays crossing the product, the processor being adapted to provide time related correction signals for each ray to the analyser to equalize the transit times to a predetermined nominal value thereby to improve the accuracy of the dimensional parameters of the product being measured.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 16 shows the results of imaging analysis to display contaminants in the finished product such as iron filings or sand particles and the like.

DETAILED DESCRIPTION

Preferred embodiments of the invention are shown in FIGS. 1-16 to which reference will be made to the following discussion.

Where similar parts of the apparatus to be described are used throughout the drawings, these will be referred to with identical reference numbers.

Figure 1:
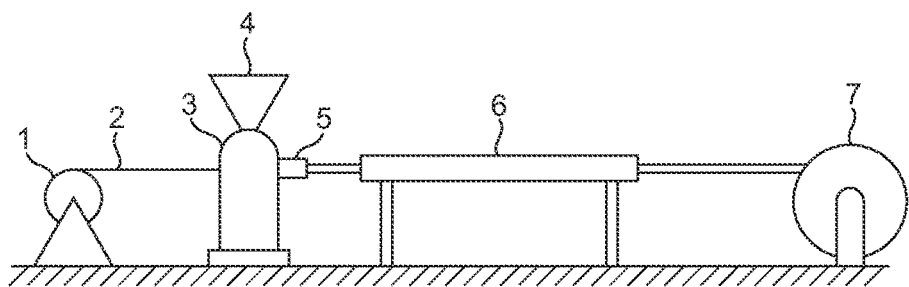
FIG. 1 is a side view of an extrusion line for manufacturing an electrical cable.

With reference to FIG. 1, this illustrates an electrical cable extrusion line comprising a payoff 1 extruding a metallic conductor 2 made of copper, aluminum or steel into an extruder 3.

Rubber or plastic material is introduced into a hopper 4 in the cold state, heated in the extruder 3 which extrudes resulting hot plastics onto the metallic conductor 2 through a forming die-head 5.

The insulated cable is thereafter hauled through a water cooling section 6 and wound on take-up 7.

A non-metallic pipe or tube extrusion line is similar in many respects to a cable line but in which a payoff 1 is not required as the tube or pipe will be formed inside the extruder 3.

Measurement of cable parameters such as diameter/wall thickness and/or eccentricity will take place at positions either before or after the water cooling section 6.

Figure 2:
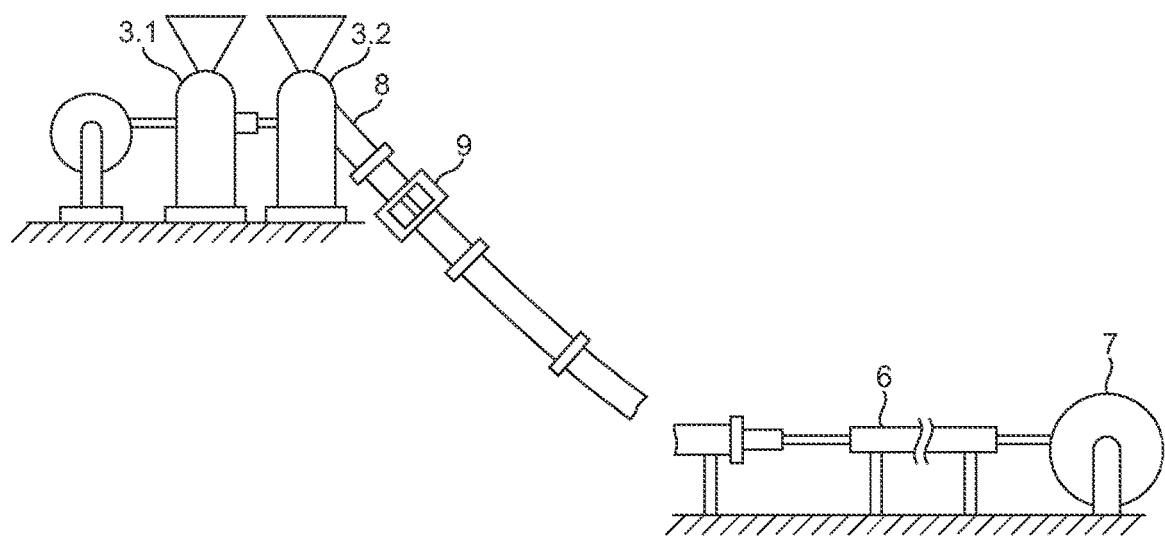
FIG. 2 shows a side view of a double or triple extrusion line for coating the inner metallic core of an electrical cable.

In FIG. 2 there is shown a double or triple extruder line 3.1, 3.2 in which two or three extrusions take place in series and at the same time.

These extrusion lines manufacture electric cables for special applications such as for use in under sea water communications or high voltage transmission cables.

In the latter case, the cable is extruded in a catenary tube 8 in which the cable installation is heat cured in a steam or nitrogen atmosphere, before it exits into the water cooling section 6 and take-up 7.

Measurements of cable parameters in these lines will take place through a specially constructed 'see through window box 9'.

Figure 3:
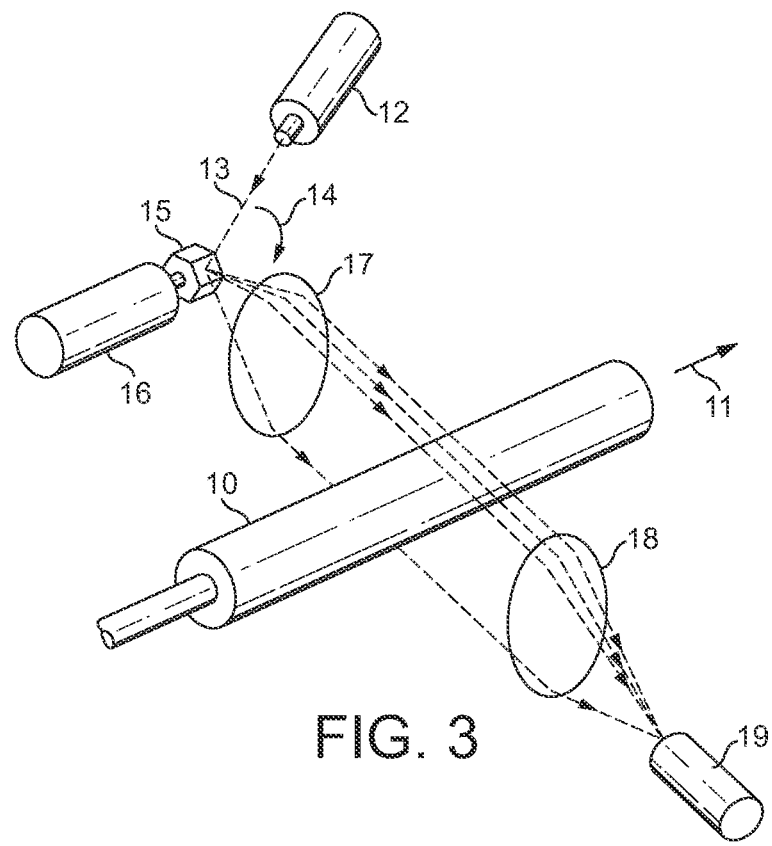
FIG. 3 illustrates the application of the invention to a tube pipe or electrical cable being extruded in a linear direction along their axes of travel.

To illustrate the employment of the invention in more detail, reference is made to FIG. 3 in which a product 10, which, in embodiments, is a tube, pipe or electric cable, is shown being extruded in a linear direction along the axis of the product as shown by arrow 11.

A Terahertz (THz) radiating unit 12 provides a ray 13 directed onto a reflecting surface.

The reflecting surface is either a single-sided mirror, or one facet of a polygonal mirror drum driven in a rotating manner 14 by means of an electric motor 16, creating a rotating mirror 15.

This rotation in effect scans the ray 13 across the diameter of a lens 17 which produces a curtain of parallel scans of rays across the product 10.

A lens 18 is positioned on the opposite side of the product 10 to receive the THz rays from the lens 17.

A THz sensor 19 and an imaging analysis unit (not shown) analyses the oncoming beams from lens 18.

Figure 4:
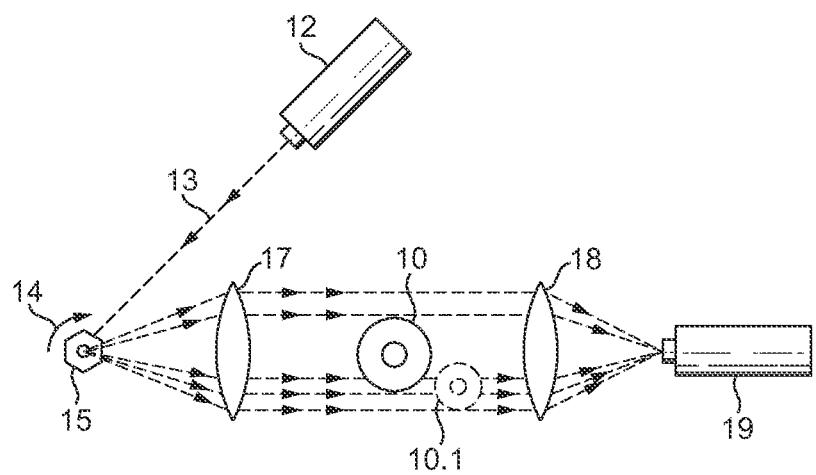
FIG. 4 shows a different view of the arrangement shown in FIG. 3 wherein the travelling product is shown in cross-section to better illustrate how the parallel rays of THz radiation are produced from a single THz radiation source.

FIG. 4 is a cross-sectional view through the product 10 of FIG. 3, to better illustrate the passage of the THz radiation from the unit 12 to rotating mirror 15 the lenses 17, 18 and the THz sensor 19.

As will be evident from FIG. 4 it is possible using the system described, to ascertain the diameter, wall thickness and/or eccentricity of the product 10 in a horizontal plain.

It is also possible as will be readily appreciated to provide a similar arrangement in which measurements may be taken in a vertical plane.

An important reason in accordance with the invention for scanning parallel THz radiation across the product 10 in its path of travel in free space, is that a measurement may take place irrespective of the position of the product 10 within the curtain of parallel rays of THz radiation, see for example position 10.1 of the product shown in FIG. 4.

As alluded to, this method is useful as firstly the product does not have to be guided by contact rollers and secondly, it is important in an application where the object is in a hot state, rendering the same, difficult to guide in any manner or form.

Figure 5:
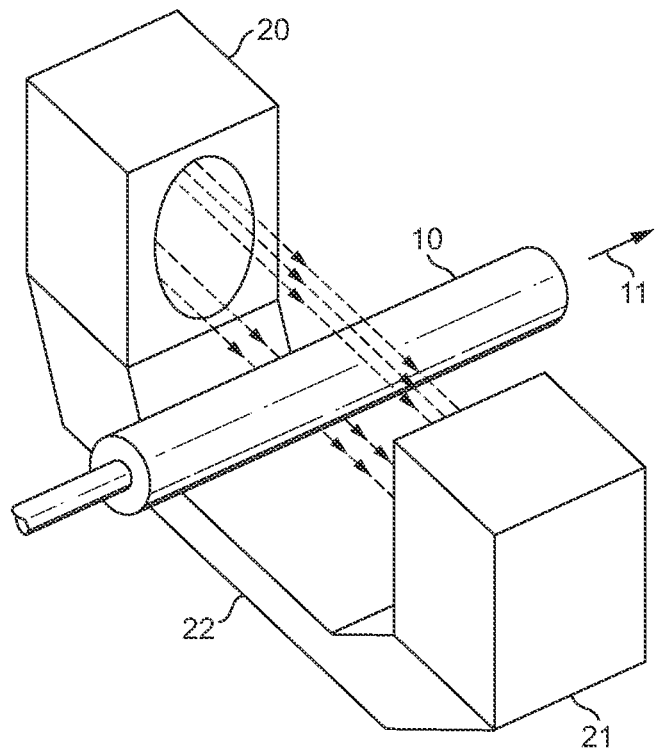
FIG. 5 illustrates in schematic view an extruded product in its path of travel and being subject to measurements by means of THz radiation in accordance with the invention.

FIG. 5 shows the product 10 in a position between a transmitter 20 of THz radiation and a receiver 21, mounted on a cradle base 22.

The transmitter 20 houses a THz radiation unit, the motor-driven scanning mirror drum device, i.e. a rotating mirror 15, and lens 17 shown in previous figures, thereby to produce a parallel curtain of THz rays across the space between transmitter 20 and receiver 21.

The receiver 21 houses the lens 18, THz sensor 19 and the THz imaging analysis unit circuit, determining the "transit time" of each successive THz ray through the insulating part of the product 10 under test and outputs the values on a processing unit 23 (shown in FIG. 10) which is connected to receiver 21, either by wire or wireless connection.

Figure 10:
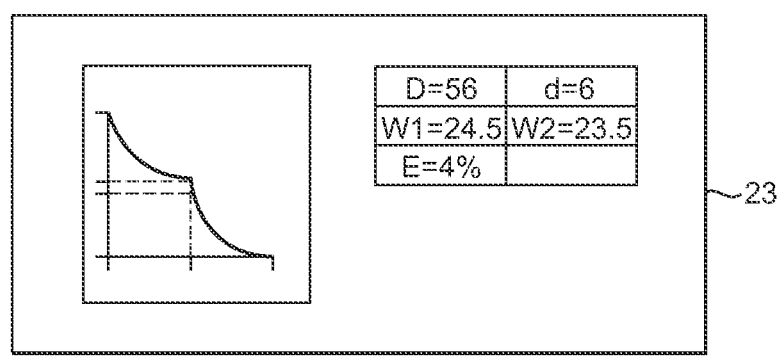
FIG. 10 illustrates a processing unit displaying details of the measurements of an electrical cable under test including a matrix image and values of diameter wall thickness and eccentricity thereof.

The processing unit 23 computes the imaging analysis information and produces matrix images and values of overall diameter (D) inner diameter (d) and eccentricity (E) of the product under test, as shown in FIG. 10.

Figure 6:
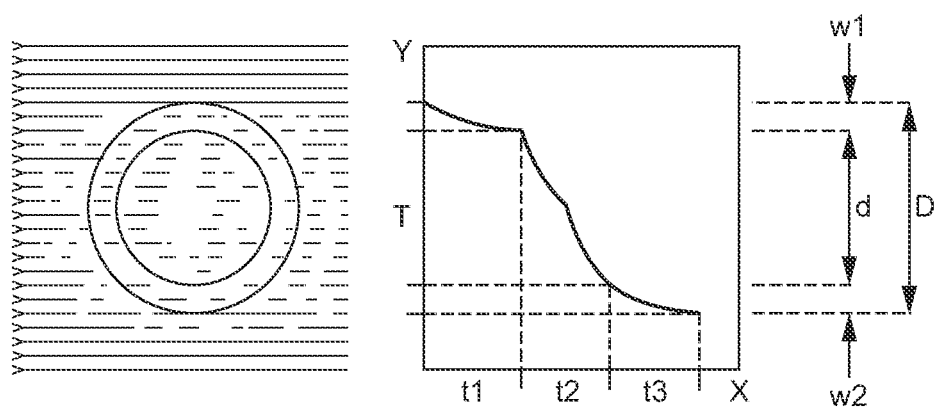
FIG. 6 shows the matrix image of the cross-section of an extruded tube or pipe and in graphical form the results of the measurement of its wall thickness according to an embodiment of the invention.

In FIG. 6 the results of measurement of the cross-section of a tube under test is shown in which (D) is the overall diameter (d) is the inner diameter. The horizontal X-axis of the graph, displays the "transit times" of the THz radiation t1, t2, t3 and the vertical Y-axis of the graph represents the scanning time T.

The wall thickness of the tube is denoted by W1 and W2 in the vertical axis and the average thickness may be computed from the formula (W1+W2)/2.

Figure 7:
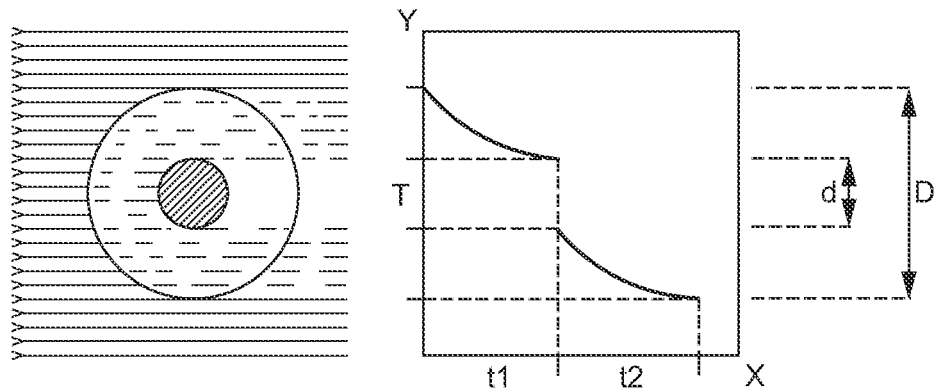
FIG. 7 shows similar results to those shown in FIG. 6 but in this case measurement is of the overall diameter of an extruded electrical cable and the diameter of the cable core.

FIG. 7 shows similar results to those shown in FIG. 6 but wherein the cross-section is of a cable in which t1 and t2 are the "transit times" along the x-axis of the graphical representation shown and the scanning rate T in the vertical y-axis.

(D) represents the overall diameter of the cable and (d) represents the electrical conductor diameter (core) of the cable under test.

Figure 8A:
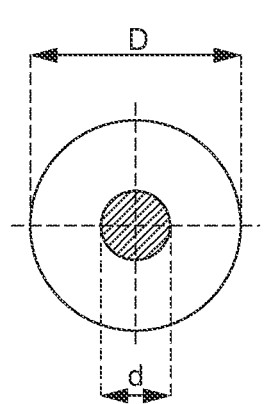
FIG. 8A shows the cross section of a moving cable in which the core of the cable is travelling concentrically.
Figure 8B:
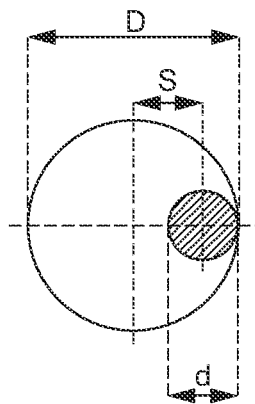
FIG. 8B shows the cross section of a moving cable in which the cable is non-concentric which positional eccentricity can be measured in accordance with the apparatus of the invention.

FIGS. 8A and 8B illustrate how the cable eccentricity may be calculated, wherein cable eccentricity may be defined by the equation:

$$E = S/(D/2 - d/2) \times 100\%$$

Where (E) is eccentricity, (D) overall diameter, (d) is core diameter and (S) is distance between the centers of (D) and (d).

In FIG. 8A, S=0 therefore E=0 which means that the cable is concentric.

In FIG. 8B, S=D/2−d/2, therefore E=1×100=100%, which means that the cable has 100% eccentricity and, in practice, is unusable.

In a practical example let, D=56 mm, d=6 mm and S=1 mm.

Using the eccentricity equation given above, then E=1/25× 100%, i.e. 4% which would be an acceptable result.

The measurements of (D), (d) and (E) are displayed on the processing unit 23 as referred to above with reference to FIG. 5.

In the case of correction of cable eccentricity as described, this if necessary may be achieved preferably by adjustments to the extrusion forming die-head 5.

Figure 9:
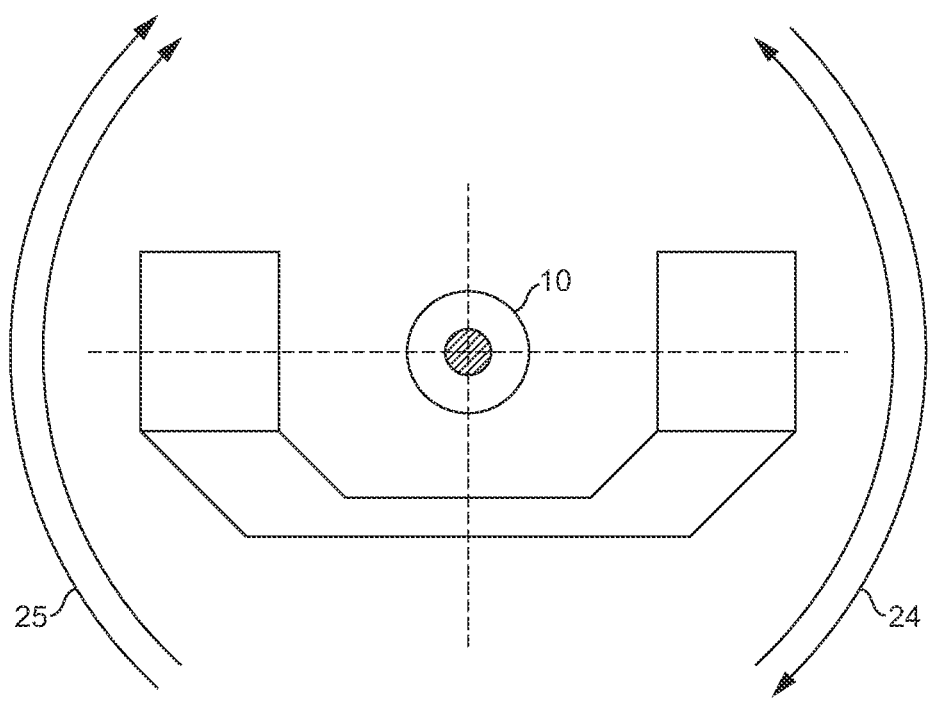
FIG. 9 illustrates a device for obtaining a multiplicity of measurements of the travelling extruded product in accordance with the invention.

FIG. 9 shows an arrangement wherein the transmitter 20 of THz radiation and the receiver 21 for the radiation after passing through product 10 may be mounted on a rotatable cradle base 22, (see FIG. 5) which is able to perform the following functions.

The cradle base 22 is able to oscillate about the center of the travelling product 10 in a "to and fro" rotation and also in a continuous circular mode, illustrated by the arrows 24, 25.

Non-contact transmission from a controller (not shown) to the imaging analysis circuit provided in the receiver 21, permits communication of all functions that are being operated in the receiver 21 as well as the transmitter 20.

The invention as described in the preceding embodiments thereof, is able to apply control functions to extrusion lines, whereby by measuring the diameter deviations, feedback can be applied to make adjustments to the extrusion line production speed, in order to maintain the diameter of the cable or tube within required specifications.

In specific cases, the extruder output may also be used for the same purpose. The cable eccentricity may be corrected as referred to already by adjustments to the forming die-head 5, of the extruder 3.

Further preferred embodiments of the invention are shown in FIGS. 11-16.

Figure 11:
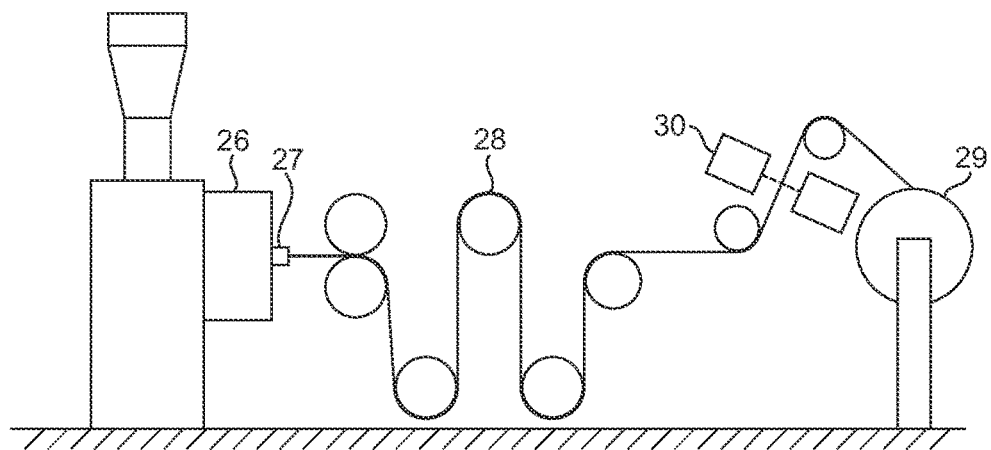
FIG. 11 shows a side view of a plastic extruder similar to the extruder shown in FIG. 1 modified to extrude flat products.

FIG. 11, shows a side view of a plastic extruder 26 similar in operation to the extruder (3) in FIG. 1 but having a modified forming die-head 27, designed to extrude flat sheets of rubber or plastic materials including, polyethylene, nylon, PVC, acrylic and the like, in varying thicknesses and widths.

The hot material exiting from forming die-head 27 enters a cooling zone 28, comprising a number of cooling rolls or calendars, which also determine the thickness of the sheet. The width of the sheet is determined by "side slitters" not shown. The sheet progresses to the take-up 29 and measurements of thickness and width, as well as quality control, may take place in position 30.

Figure 12:
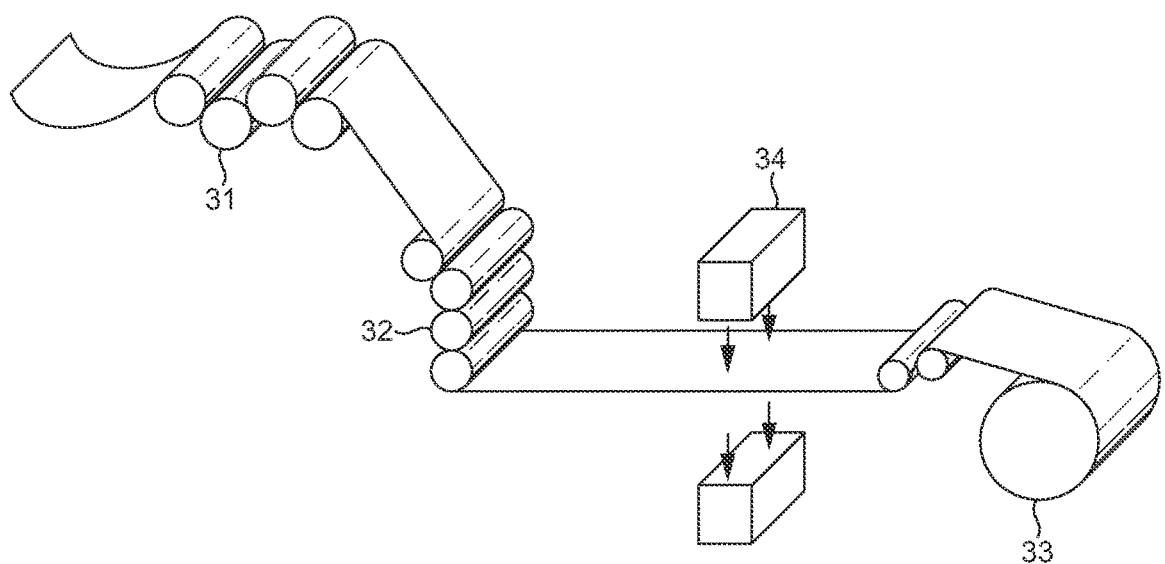
FIG. 12 illustrates a paper sheet producing line.

FIG. 12 shows a "paper sheet producing line" whereby, paper exits from the Pulping Machine (not shown) and enters a drying zone 31 made up from heated drums. Next, the paper moves on to a coating zone 32 thereby it may be coated with various chemicals or plastic materials, depending on application requirements.

At this point, the paper is "thickness sized" by pressure rollers and the width is determined by "edge slitters" (not shown).

The finished paper sheet is wound on to a drum 33 and measurements of thickness and width and quality control, may take place in position 34.

Figure 13A:
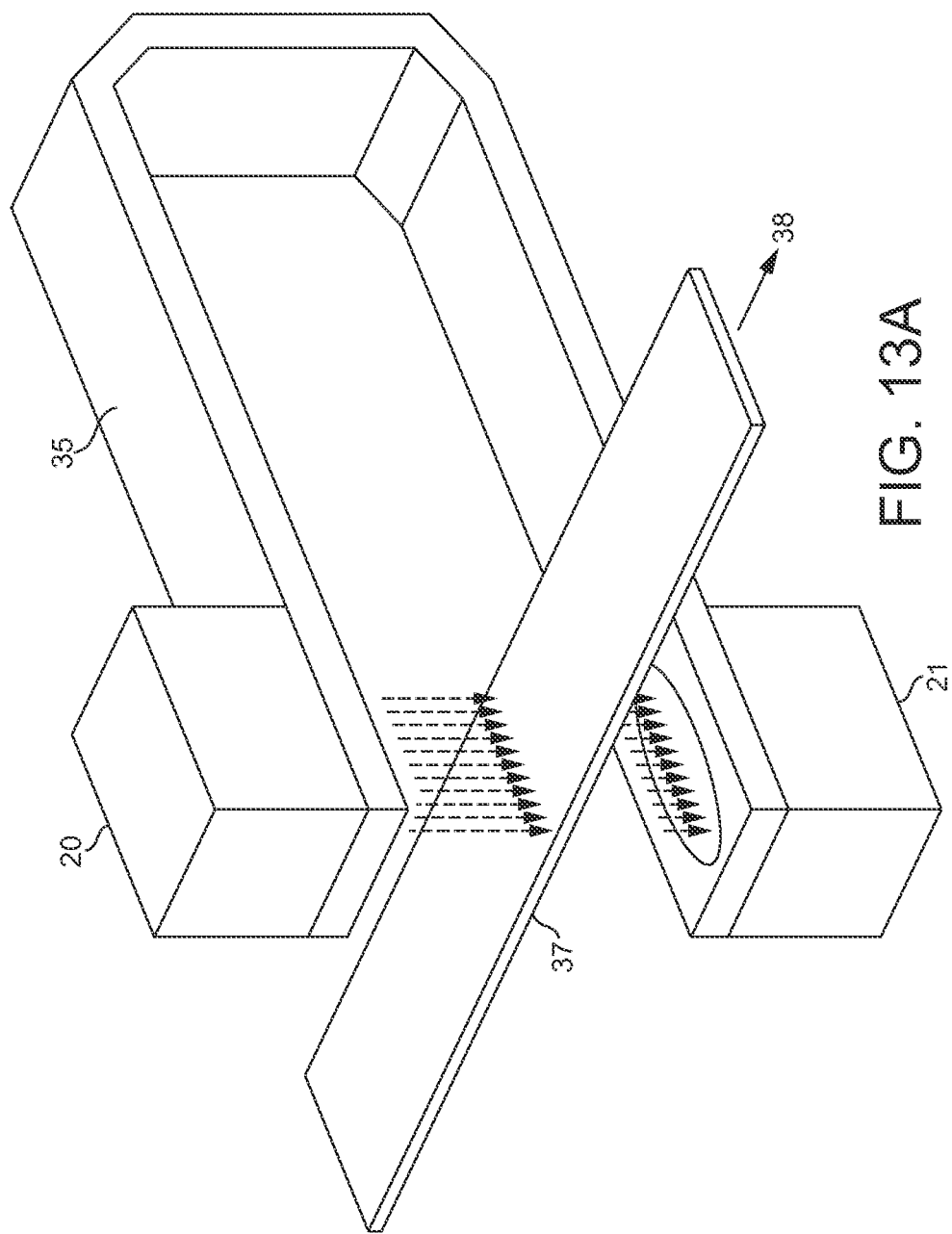
FIG. 13A shows an arrangement similar to FIG. 5 mounted on a C-frame thereby to continuously scan the complete surface area of a flat product.

FIG. 13A, shows an "installation," comprising a transmitter 20 and receiver 21 (shown in FIG. 5) mounted on a C-Frame 35, whereby the curtain of parallel rays of said THz radiation (page 3, lines 9-11) thereof, is scanning continuously the complete surface area of a flat product 37, in its path of travel 38.

In this case, the span of the curtain of parallel rays of said THz radiation, is adequately wide, thereby to cope with the full width of product 37.

Figure 13B:
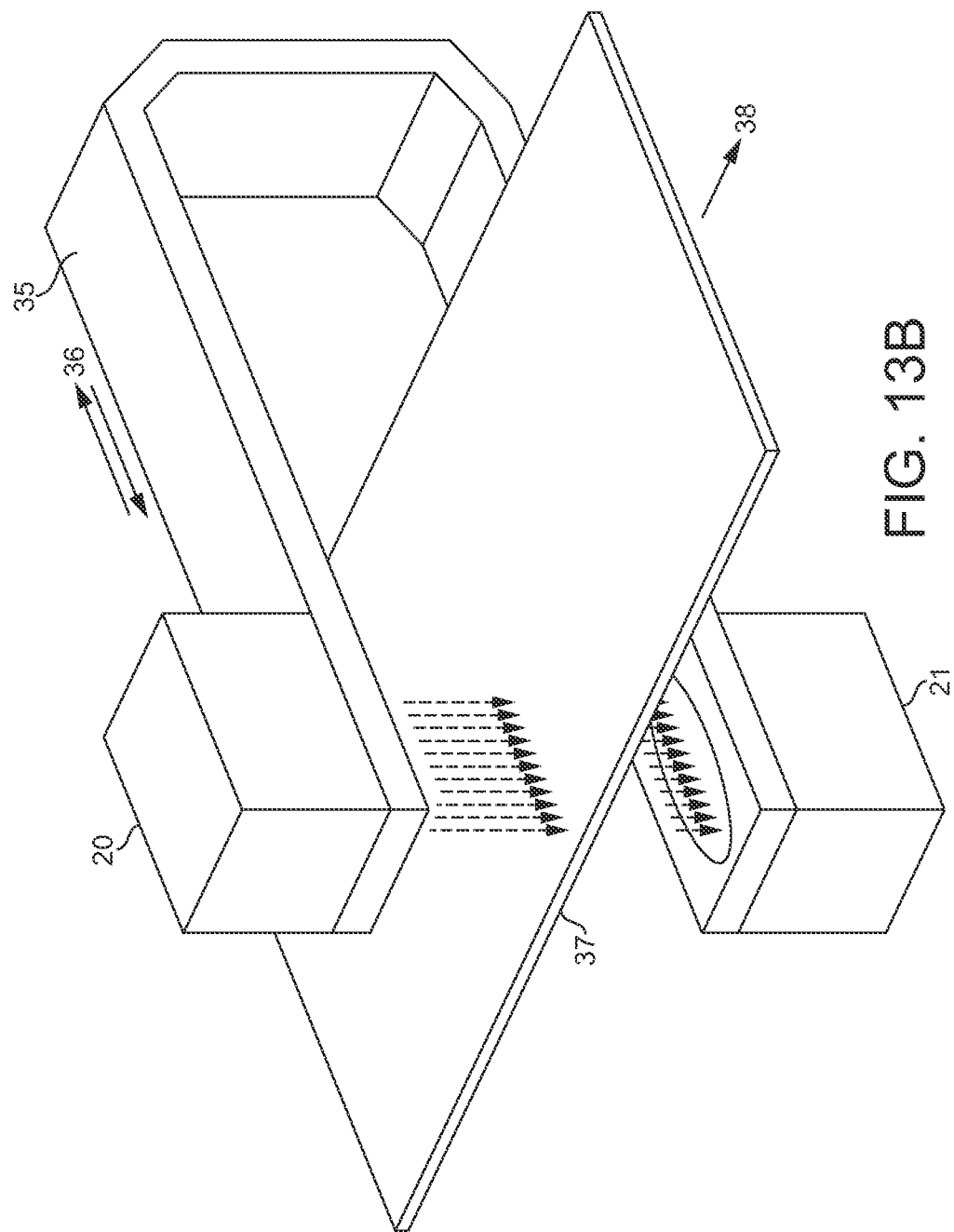
FIG. 13B illustrates the arrangement of FIG. 13A modified to cater for scanning wide products and provided with a reciprocating motion to achieve that end.

In applications of exceptionally wide products 37, FIG. 13B, it is possible to mount additional said "installations" (which comprise a receiver 21 and transmitter 20 as shown in FIG. 5) on the C-frame (not shown), thereby, to provide, said complete scanning coverage, to the full width of the said product 37 under manufacture, on a continuous basis.

In practice a more economical option may be considered, thereby to provide a single "installation" (which comprises a receiver 21 and transmitter 20 as shown in FIG. 5) on the C-Frame, as it may be adequate, particularly when, the majority of production requirements, are for product widths, which fall within the span of the curtain of parallel rays of said THz radiation.

In some applications processing wide products 37, FIG. 13B it is possible that intermittent, or random checks of dimensional parameters and or of quality control, are sufficient to ensure minimum acceptable standards for these products. In these cases a single "installation" (which comprises a receiver 21 and transmitter 20 as shown in FIG. 5) on the C-Frame, may be employed, whereby, the said C-Frame is set, in a "Transverse Reciprocating" motion 36, across the width of the product 37, thereby, to facilitate intermittent, or randomized measuring coverage of said product.

Single or multiple "installations" (which comprise a receiver 21 and transmitter 20 as shown in FIG. 5), are connected to the processing unit 23 (FIG. 10), either by wire or preferably by wireless communication, thereby measurements of said product thickness and dimensional parameters of the flat sheet as well as quality control inspection results, are determined by imaging analysis and displayed in a matrix.

The processing unit 23 (FIG. 10), can provide complete Data Logging of several lengths of products, as may be required in cases where high quality is necessary, in the performance and application of said product.

Figure 14:
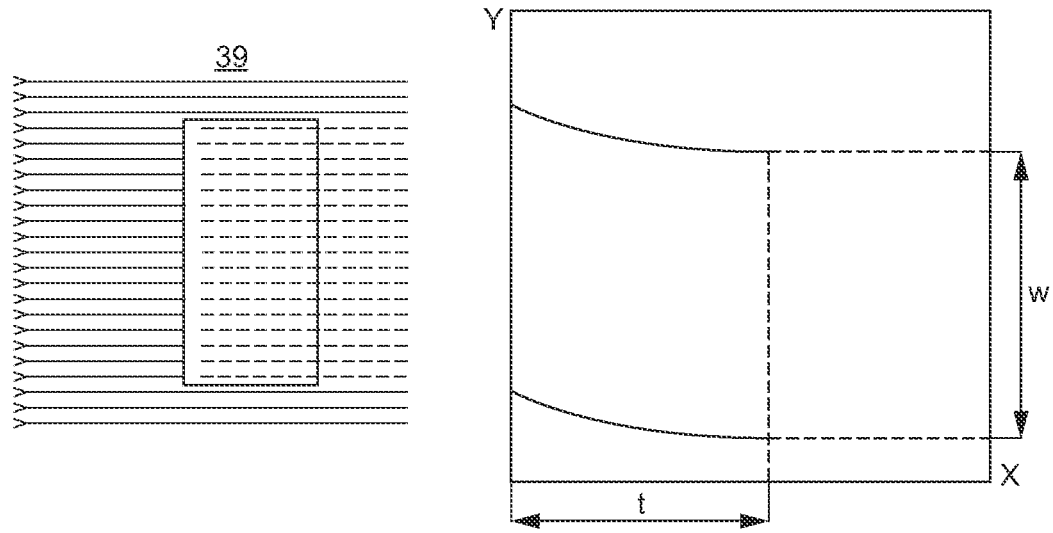
FIG. 14 shows the cross-section of a product under test together with an associated matrix in graphical format thereby to enable the imaging analysis of the product and provide a measure of its width.
Figure 15:
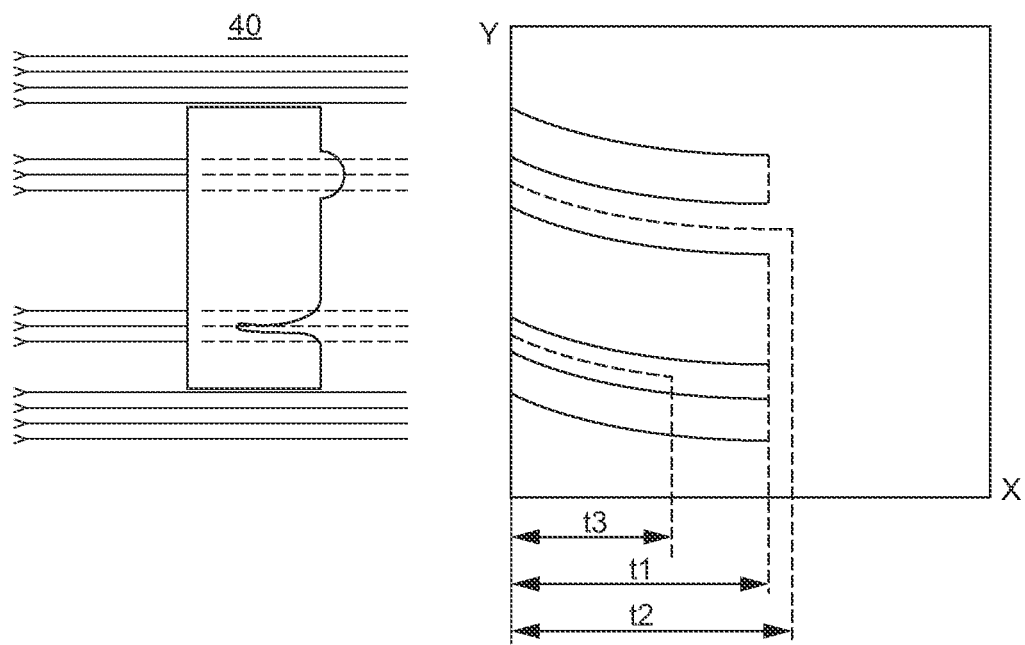
FIG. 15 shows in graphical display the resulting analysis of the emitted Terahertz radiation (THz) from the product to provide evidence of ridges or fissures in the manufactured product.

FIG. 14, shows a cross section of product 39 under test, together with the associated matrix in a graph format, whereby the thickness is represented by (t) in the x-axis and the width is represented by (w) in the y-axis, in a similar manner to the matrix shown in FIG. 6. FIG. 15 shows a product 40 with defects. The resulting analysis of the time related signals are displayed in the associated matrix thereof, the x-axis shows ridges as (t2), fissures as (t3) and (t1) as the product thickness.

Figure 16:
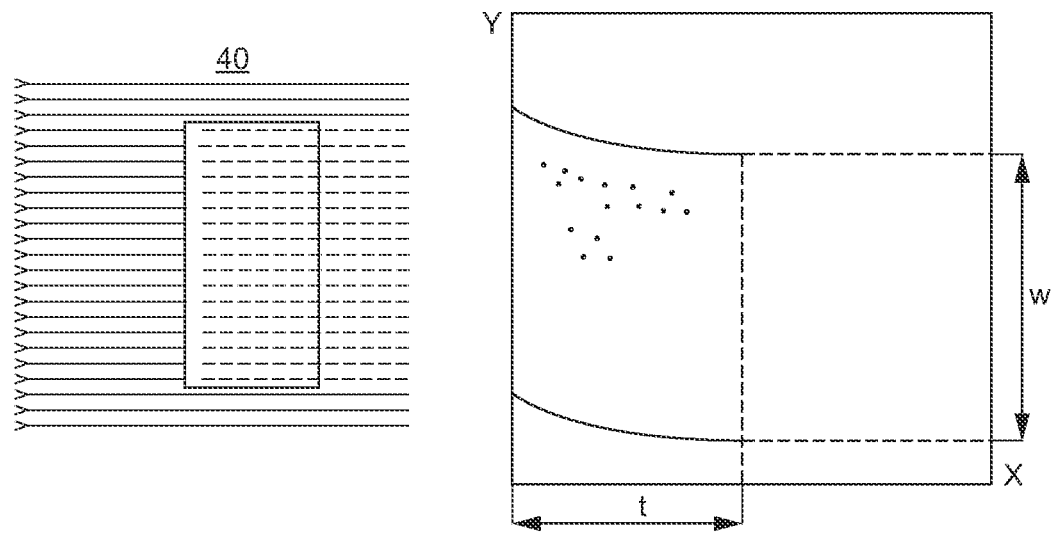

FIG. 16 shows contaminants in the product, including iron filings or sand particles and the like, displayed as dots in the associated Matrix.

With reference to what has been described above in order to achieve high accuracy in the dimensional parameter measurements of product 10, irrespective of the position of the product 10, being anywhere within the curtain of THz parallel rays 13, the following in depth analysis of the facts will be considered. It is to be noted that the analysis of the facts applies equally to Laser or LED rays.

Figure 17:
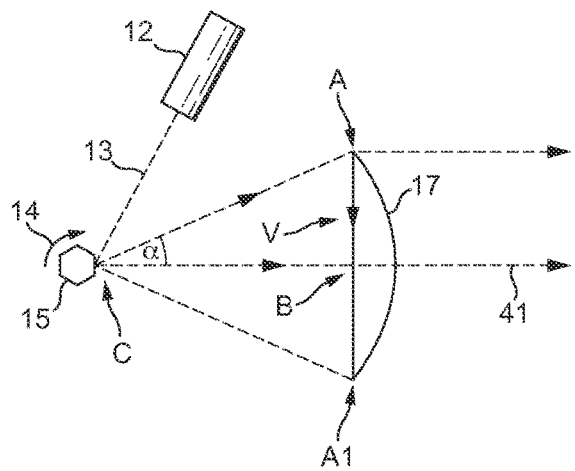
FIGS. 17 and 18 are views based on the arrangement shown in FIG. 4 to illustrate how measurement inaccuracies occur as a result of axial movement of a travelling product in its path of travel through a curtain of parallel rays of THz radiation.

FIG. 17 is an illustration in side view of the scanning section of the optical measuring system shown in FIG. 4. For clarity purposes, let us assume that the lens 17 is of the plano-convex type, with A A1 being the diameter and B C the focal length of the lens 17.

Each successive ray 13, rotating in direction 14, comes in contact with the lens 17 at point A, whereby the lens 17 effectively "bends" the rays 13, from a rotating mode to a linear mode, thus forming a curtain of THz rays, parallel to the centerline 41.

The fact of "bending" rotating rays 13 into a parallel linear mode, results in a non-linear scanning speed (V) of each successive the ray 13, across the diameter A A1 of the lens 17.

Figure 18:
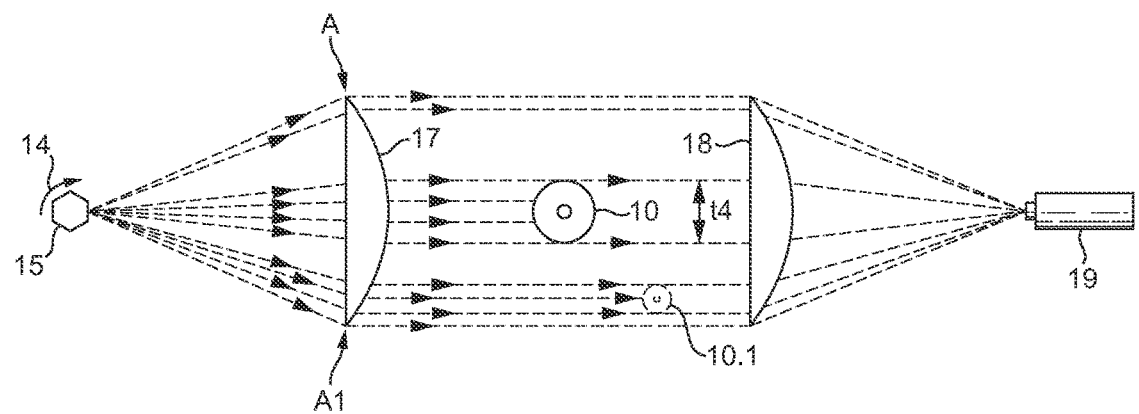

FIG. 18 shows the optical measuring system of FIG. 4 further illustrating the principle of measuring the dimensional parameters of the product 10 and the reasons why inaccuracies in dimensional measurement occur due to axial movement of the product in its path of travel.

Each successive ray 13, travelling across the diameter A A1 of the lens 17 at speed (V), will take a transit time (t4) crossing the product 10 from edge to edge.

Time (t4), is a function ($f$) of the diameter or size of the product 10, thus if (D) is the diameter or size of the product 10, then t4=f (D/V) and D=f (V×t4).

The non-linear scanning speed (V) of the rays 13 travelling across the product 10, produces varying transit time periods (t4) being measured over the product 10, depending on the position of the product 10, within the curtain of parallel THz rays 13, and therefore inaccurate parameter measurements for the product 10.

We will now show, by an example, the errors that occur by the non-linearity of the transit speed (V) across the lens 17 from A to A1.

Let:

the diameter A A1 of lens 17=30 mm the focal length B C of lens 17=80 mm the Angle between B C and A C=($a$)

Considering the right angled triangle, formed by A, B, C, we have AB=BC×tan($a$), Therefore:

$$\text{Angle}(a)=\tan^{-1}(AB/BC)=\tan^{-1}(15/80)=10.6°\text{Degrees}$$

The scanning speed (V) of ray 13 across points A B of lens 17 is the derivative of tan($a$), therefore:

$$V=d/d(a)(\tan(a))=1/\cos^2(a)$$

Hence, the speed of each ray 13 at point A (edge) of lens 17 is:

$$(VA)=1/\cos^2(10.6°)=1.035$$

The speed at point B (center) of lens 17 is:

$$(VB)=1/\cos^2(0°)=1/(1)^2=1.00$$

The speed difference of ray 13 between point A (edge) and point B (center), of lens 17 is:

$$VA-VB=1.035-1.000=+0.035$$

Therefore, the speed of the ray 13 VA, is faster at the (edge) A of lens 17, than speed VB at the (center) B of lens 17.

Due to the symmetrical disposure of lens 17, the speed of ray 13 at the other edge A1 of lens 17, VA1, will equal to VA, thus, VA1=VA=1.035. Therefore, the non-linearity error in the scanning speed (V) across the diameter A, A1 of lens 17 is 3.5%.

Accordingly, as the scanning speed (V) of the rays 13, is faster towards the edges, A and A1 of the lens 17 and slower in the middle B of the lens 17, said transit time (t4) of the rays 13 across the product 10, is shorter near the edges A and A1 and longer in the middle B of the lens 17.

As the method of measurement of the diameter or size of product 10, is transit time related, the effect of shorter transit time (t4) near the edges A or A1 of the lens 17, will result in the product 10, appearing to be smaller in diameter or size.

If the product 10 is positioned near the middle B of the lens 17, it will appear to be larger, as the transit time (t4) across the product 10 will be longer.

In order to improve the accuracy in the application of this invention, the non-linearity error caused by the scanning speed (V) as shown in our previous example, must be removed.

Disclosed herein is a polynomial equation (P), consisting of the following variables and coefficients:
- (e): The angle (a) between BC and AC of the triangle ABC;
- (f): The location of the product 10 within the curtain of THz rays 13
- (g): The transit time period (t4) of each successive ray 13 travelling across the product 10
- (h): The physical parameters of lens 17

Items (e), (f), (g), are variable values, while (h) represents preset constant values.

The polynomial (P) calculates, by software, the values of (e), (f) and (g) and determines a correction value (F) which is a function ($f$) of (P).

Thus, $(F)=f(P)(e,f,g,h)$

Lens 18 receives the THz rays 13 and focuses the rays on to sensor 19 and imaging analysis unit referred to hereinbefore with reference to FIG. 3, whereby the polynomial (P) is used to apply within the processing capability of the analyzer unit a continuous stream of correction data to the software of the analyzer unit thereby creating a correction value (F), for every successive ray 13, thus eliminating all instantaneous optical and positional errors of the product 10, travelling linearly anywhere within the curtain of THz rays.

Returning previous example of the triangle ABC, we now show how the correction is applied to this case:
- (i) Speed of ray 13 at point A (edge) of lens 17, VA=1.035 Correction to be applied (F)=0.035 therefore corrected speed is:

$VA=1.035-0.035=1$

- (ii) Speed of ray 13 at point B (center) of lens 17, VB=1 Correction to be applied (F)=0, therefore corrected speed is:

$VB=1-0=1$

Hence VA=VB

Also, as pointed out earlier, due to the symmetrical disposure of lens 17:

$VA=VB=VA1$

- (iii) Appropriate corrections (F) are applied to the scanning speed V of successive rays 13, ensuring that said speed V remains linear, as the rays 13, travel across the diameter A, A1 of the lens 17.

The dimensional accuracy attained by the present invention is one (1) micron (1 micron=1/1,000 mm) which is a considerable improvement over the accuracy obtainable with similar optical measuring apparatus known to the applicant.

Thus in U.S. Pat. No. 3,765,774 to Petrohilos, while there is no specific claim to any "measurement accuracy" there is a reference to "readout tolerances of +/−0.001 inch" or 0.002 inch overall.

Converting 0.002 inch into microns, 1 inch=25 mm, hence 0.002 inch=0.050 mm or 50 microns much in excess of the 1 micron "tolerance" achieved by the present invention.

In view of the 1 micron accuracy, the present invention is particularly suitable in dimensional applications in the range of 80-150 microns, such as optical fibers, fine wires and the like, and also in close tolerance data transmission cables, LAN, CAT 6 & 7 and CATV, as well as in the manufacture of High Voltage Power cables.

The advantage of the present invention is further shown in flat product applications such as plastic sheets, tapes, films, paper production and the like FIG. 11 and FIG. 12, whereby the curtain of THz rays, in which all rays are individually of 1 micron accuracy, perform correct measurements of the flat sheet width.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. An apparatus for non-contact measurement of the dimensional parameters of an elongated, non-guided industrial product being extruded continuously in free space, comprising:
    a source of terahertz radiation;
    a scanner system for scanning the product with a curtain of parallel rays of said radiation across the product from one side thereof;
    a sensor for detecting the composition of emitted radiation following its passage through said extruded product, positioned opposite said scanner system; and
    an image analyzer unit operatively associated with the sensor for performing time related imaging analysis of said emitted radiation thereby to determine said dimensional parameters, characterized in that said analyzer incorporates a processor for computing correction data representative of variation in the transit times between the rays in different positions in the curtain of parallel rays crossing the product as its position varies therein, due to swaying in its path of travel or other factors, said processor being adapted to provide time related correction signals that account for the variation in transit times between the rays for each ray and the movement of the product to said analyzer to equalize the transit times of the rays crossing the product thereby to improve the accuracy of the dimensional parameters of the product being measured.

2. An apparatus as claimed in claim 1 further comprising a rotating mirror and a first lens for receiving successive rays of terahertz radiation from said mirror to produce said curtain of parallel rays of terahertz radiation for scanning the product, wherein the terahertz radiation is directed onto said rotating mirror.

3. An apparatus as claimed in claim 1 further comprising a second lens for receiving the terahertz radiation after passage through the product and for focusing the rays onto said sensor.

4. An apparatus for non-contact measurement of the dimensional parameters of an elongated, non-guided industrial product such as a rubber or plastic tube or electrical cable, being extruded continuously in free space, comprising:

a terahertz radiation unit;

a rotating mirror for scanning terahertz rays emitted from a point source across a first lens to produce a curtain of parallel terahertz rays, through which the product travels linearly at right angles thereto, said rays after passing through said insulating material being collected by a second lens, and focused at a terahertz sensor; and an image analyzer operatively associated with the sensor for performing time related imaging analysis of terahertz rays penetrating said insulating material to provide a matrix image from which to determine said dimensional parameters of the product, characterized in that said analyzer incorporates a processor for computing correction data representative of variation in the transit times between the rays in different positions in the curtain of parallel rays crossing the product as its position varies therein, due to swaying in its path of travel or other factors, said processor being adapted to provide time related correction signals that account for the variation in transit times between the rays for each ray and the movement of the product to said analyzer to equalize said transit times to a predetermined nominal value thereby to improve the accuracy of the dimensional parameters of the product being measured.

5. The apparatus as claimed in claim 4, further comprising an enclosure for passage of the product in its path of travel in a hostile environment of high temperature and pressure, said enclosure comprising a transparent window box to allow the passage of the terahertz radiation therethrough for measurement in said imaging analysis device.

6. The apparatus as claimed in claim 5 further comprising an oscillating mechanism for effecting oscillation of the non-contact measurement unit, including the source of terahertz radiation, scanner system, and sensor, around the axis of said product in its path of travel to collect a set of data relating to the diameter/wall thickness and/or eccentricity of the product.

7. The apparatus as claimed in claim 6 configured to oscillate during use, wherein said oscillation comprises either a backwards and forward motion around the axis of the product or a continuous rotational mode around the product, to log a set of data relating to the diameter, wall thickness and/or eccentricity of the product under test.

8. The apparatus as claimed in claim 4 further comprising a correction device for applying a corrective action to the extrusion line to vary the production speed, extruder volume output and/or adjustment of the forming die-head of the extruder either automatically or manually, in order to maintain a predetermined required product specification.

9. The apparatus as claimed in any claim 4 wherein the curtain of parallel rays of said terahertz radiation is used to scan a flat product, which is equal or less in width to the span width of the curtain of parallel rays of terahertz radiation, in order to inspect the complete area of the said product.

10. The apparatus as claimed in claim 9, wherein said apparatus, including the source of terahertz radiation, scanner system, and sensor, is mounted on a C-Frame, which is adapted to move reciprocally, in a transverse manner, at right angles to the linear path of travel of the elongated flat product, whereby a product wider than the width span of the said curtain of parallel rays of terahertz radiation, may be scanned, by moving the C-Frame in a reciprocating forward and reverse motion across the width of the flat product.

* * * * *